United States Patent
Binnekamp et al.

(10) Patent No.: US 10,850,126 B2
(45) Date of Patent: Dec. 1, 2020

(54) SYSTEM AND METHOD FOR GUIDED ADAPTIVE BRACHYTHERAPY

(75) Inventors: Dirk Binnekamp, Borne (NL); Luis Felipe Gutierrez, Jersey City, NJ (US); Neil David Glossop, Toronto (CA); Jochen Kruecker, Washington, DC (US); Shriram Sethuraman, Briarcliff Manor, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1409 days.

(21) Appl. No.: 13/703,750

(22) PCT Filed: May 27, 2011

(86) PCT No.: PCT/IB2011/052341
§ 371 (c)(1),
(2), (4) Date: Dec. 12, 2012

(87) PCT Pub. No.: WO2012/001551
PCT Pub. Date: Jan. 5, 2012

(65) Prior Publication Data
US 2013/0102891 A1 Apr. 25, 2013

Related U.S. Application Data

(60) Provisional application No. 61/359,849, filed on Jun. 30, 2010.

(51) Int. Cl.
*A61N 5/10* (2006.01)
*A61B 5/06* (2006.01)
(Continued)

(52) U.S. Cl.
CPC ............ *A61N 5/1039* (2013.01); *A61B 5/062* (2013.01); *A61B 5/065* (2013.01); *A61B 6/02* (2013.01);
(Continued)

(58) Field of Classification Search
CPC . A61B 2019/5261; A61B 5/062; A61B 5/065; A61B 6/02; A61B 8/12;
(Continued)

(56) References Cited

U.S. PATENT DOCUMENTS 5,860,909 A * 1/1999 Mick ................. A61M 37/0069
600/7
6,129,670 A * 10/2000 Burdette et al. .............. 600/427
(Continued)

FOREIGN PATENT DOCUMENTS

WO WO200113060 2/2001
WO WO2009156893 12/2009
WO WO2010011844 1/2010

OTHER PUBLICATIONS

E.E. Ahunbay, et al., "Online Adaptive Replanning Method for Prostate Radiotherapy", Oncology, online pub. Apr. 2010, one page.
(Continued)

Primary Examiner — Amelie R Davis
(74) Attorney, Agent, or Firm — Sherry Austin

(57) ABSTRACT

A system and methods for adaptive placement of a treatment element include a placement device (134), and a localization system (120) configured to track progress of the placement device such that a position of a treatment element (146, 132) placed by or to be placed by the placement device is stored in memory. A computer system (142) includes a program (104) implemented in computer readable storage media and configured to compute an effect of the treatment element at the position and determine whether a dosage amount has been achieved by the treatment element for treatment of an organ.

20 Claims, 3 Drawing Sheets

(51) Int. Cl.
*A61B 6/02* (2006.01)
*A61B 8/12* (2006.01)
*A61B 34/20* (2016.01)

(52) U.S. Cl.
CPC ............... *A61B 8/12* (2013.01); *A61N 5/103* (2013.01); *A61N 5/1007* (2013.01); *A61N 5/1048* (2013.01); *A61N 5/1071* (2013.01); A61B 2034/2061 (2016.02); A61N 5/107 (2013.01); A61N 5/1027 (2013.01); A61N 5/1038 (2013.01); A61N 2005/1058 (2013.01)

(58) Field of Classification Search
CPC .... A61B 2034/2061; A61N 2005/1058; A61N 5/1007; A61N 5/1027; A61N 5/103; A61N 5/1038; A61N 5/1039; A61N 5/1048; A61N 5/107; A61N 5/1071
See application file for complete search history.

(56) References Cited

U.S. PATENT DOCUMENTS

| | | | | |
|---|---|---|---|---|
| 6,471,710 | B1* | 10/2002 | Bucholtz | G01B 11/005 600/229 |
| 6,505,065 | B1* | 1/2003 | Yanof | A61N 5/103 600/103 |
| 6,846,282 | B1* | 1/2005 | Ford | A61N 5/1007 600/1 |
| 2003/0065260 | A1* | 4/2003 | Cheng | A61B 8/0833 600/427 |
| 2003/0112922 | A1* | 6/2003 | Burdette | A61B 6/5247 378/65 |
| 2003/0212302 | A1* | 11/2003 | Rozenfeld | A61N 5/1007 600/1 |
| 2007/0078327 | A1 | 4/2007 | Kindlein | |
| 2008/0309326 | A1* | 12/2008 | Schechter | 324/207.12 |
| 2009/0014015 | A1 | 1/2009 | Tutar | |
| 2009/0198094 | A1 | 8/2009 | Fenster et al. | |
| 2009/0234175 | A1 | 9/2009 | Maier | |
| 2010/0067660 | A1* | 3/2010 | Maurer, Jr. | A61B 6/00 378/95 |
| 2010/0081920 | A1* | 4/2010 | Whitmore, III | A61B 34/20 600/424 |

OTHER PUBLICATIONS

C.E. Noel, et al., "An Automated Method for Adaptive Radiation Therapy for Prostate Cancer Patients Using Continuous Fiducial Based Tracking", Phy. Med. Biol., 55, 2010, pp. 65-82.

Jemal A. et al., "Cancer Statistics, 2005", CA Cancer J Clin 2005; vol. 55, No. 1, pp. 10-30.

Blake C.C. et al., "Variability and Accuracy of Measurements of Prostate Brachytherapy Seed Position in Vitro Using Three-Dimensional Ultrasound: An Intra- and Inter-Observer Study", Medical Physics, vol. 27, Issue 12, pp. 2788-2795, Dec. 2000.

Whitehead G. et al., "Automated Brachytherapy Seed Localization Using Intensity Weighted Feature Extraction Techniques", 2007 4th IEEE International Symposium on Biomedical Imaging: From Nano to Macro, Arlington, VA, 2007, pp. 1152-1155, Apr. 2-15, 2007.

Lee J. et al., "Prostate Brachytherapy Seed Localization with Gaussian Blurring and Camera Self-Calibration", Medical Image Computing and Computer-Assisted Intervention—MICCAI 2008. MICCAI 2008. Lecture Notes in Computer Science, vol. 5242, pp. 636-643, 2008.

* cited by examiner

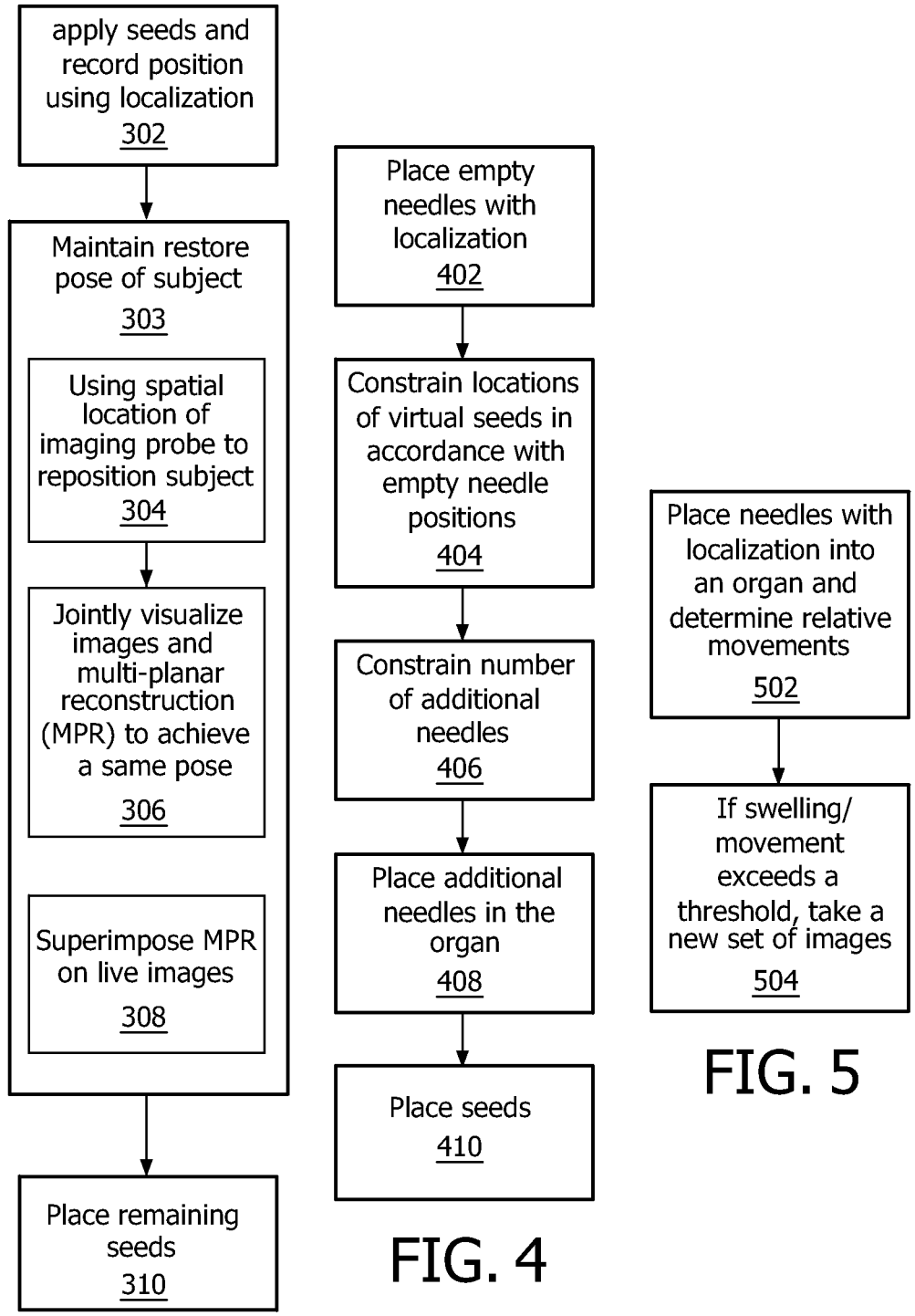

SYSTEM AND METHOD FOR GUIDED ADAPTIVE BRACHYTHERAPY

This disclosure relates to surgical systems and methods, and more particularly to a system and method for adaptively guiding medical instruments for brachytherapy and other procedures.

Treatment options for prostate cancer vary depending on the stage of the cancer, and the most widely used local treatment options include radical or partial prostatectomy, external radiotherapy, and brachytherapy. The most frequent side-effects of these treatments are erectile dysfunction and incontinence.

In brachytherapy, small radioactive seeds are placed in the prostate via needles inserted through the perineum. Transrectal ultrasound (TRUS) is used to guide the procedure. TRUS imaging allows a physician to visualize the prostate, the neighboring anatomy (urethra, bladder, etc.), and the seed-delivery needles as they are inserted into the prostate. However, the seeds themselves are not well visualized with ultrasound, so the physician cannot confirm at the time of the procedure that seed placement has been accomplished according to plan. In addition, the 2D nature of today's standard TRUS means that even though the seed delivery needles can be somewhat visualized, a precise 3D location of the needle tip is ambiguous so that physicians may not ensure accurate delivery of the needles to their target locations.

Due to these limitations of procedure guidance, seeds may be misplaced, which results in the delivery of radiation doses to regions of the prostate that are under or over the physician-prescribed dose. There have been attempts to accomplish intra-operative seed localization via improved ultrasound imaging methods and X-ray fluoroscopy, but the former have not proven to be robust, and the latter require integration of a second imaging modality which is a workflow impediment.

In accordance with the present principles, a system and methods for adaptive placement of a treatment element include a placement device, and a localization system configured to track progress of the placement device such that a position of a treatment element placed by the placement device is stored in memory. A computer system includes a program implemented in computer readable storage media and configured to compute an effect of the treatment element at the position and determine whether a dosage amount has been achieved by the treatment element for treatment of an organ. The system and methods provide accurate 3D intra-operative feedback and better guidance. This provides not just imaging but also seed placement instructions. Real-time dosimetry helps reduce underdosing (which can reduce cancer recurrence) and reduce overdosing (which may result in side effects). The system and method provide a context for seed boosting schemes.

A system for adaptive placement of a treatment element includes a placement device and a localization system configured to track progress of the placement device such that a position of a treatment element placed by the placement device is stored in memory. A computer system includes a program implemented in computer readable storage media and configured to compute an effect of at least one treatment element at the position and determine whether a dosage amount has been achieved by the at least one treatment element for treatment of an organ.

A treatment method includes computing virtual seed locations in a model of a subject to reach a target dosage plan; identifying a trajectory of a seed delivery device inserted in the subject to guide the delivery device to a target position determined in the target dosage plan; depositing a seed at or close to the target position using the seed delivery device; recording the position of the seed using a localization method; and based on actual seed locations, recomputing the virtual seed locations in accordance with the target dosage plan. Another treatment method includes placing seeds at a plurality of known locations in a subject to reach a target dosage plan; recording the locations of the seeds using a localization method; based on actual seed locations, computing virtual seed locations to provide a dosage in accordance with the target dosage plan; and depositing a seed at or close to the virtual seed locations using a seed delivery device using the localization method.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein:

FIG. 3 is a block/flow diagram showing an alternate embodiment which incorporates a combination of actual seed implants and virtual seed implants to improve planning and seed position accuracy in real-time;

FIG. 4 is a block/flow diagram for a system/method which employs empty needles to constrain real and/or virtual seed placement in accordance with an illustrative embodiment of the present invention; and FIG. 5 is a flow diagram showing a system/method for an organ swelling adaptation in accordance with an illustrative embodiment of the present invention.

Figure 1:
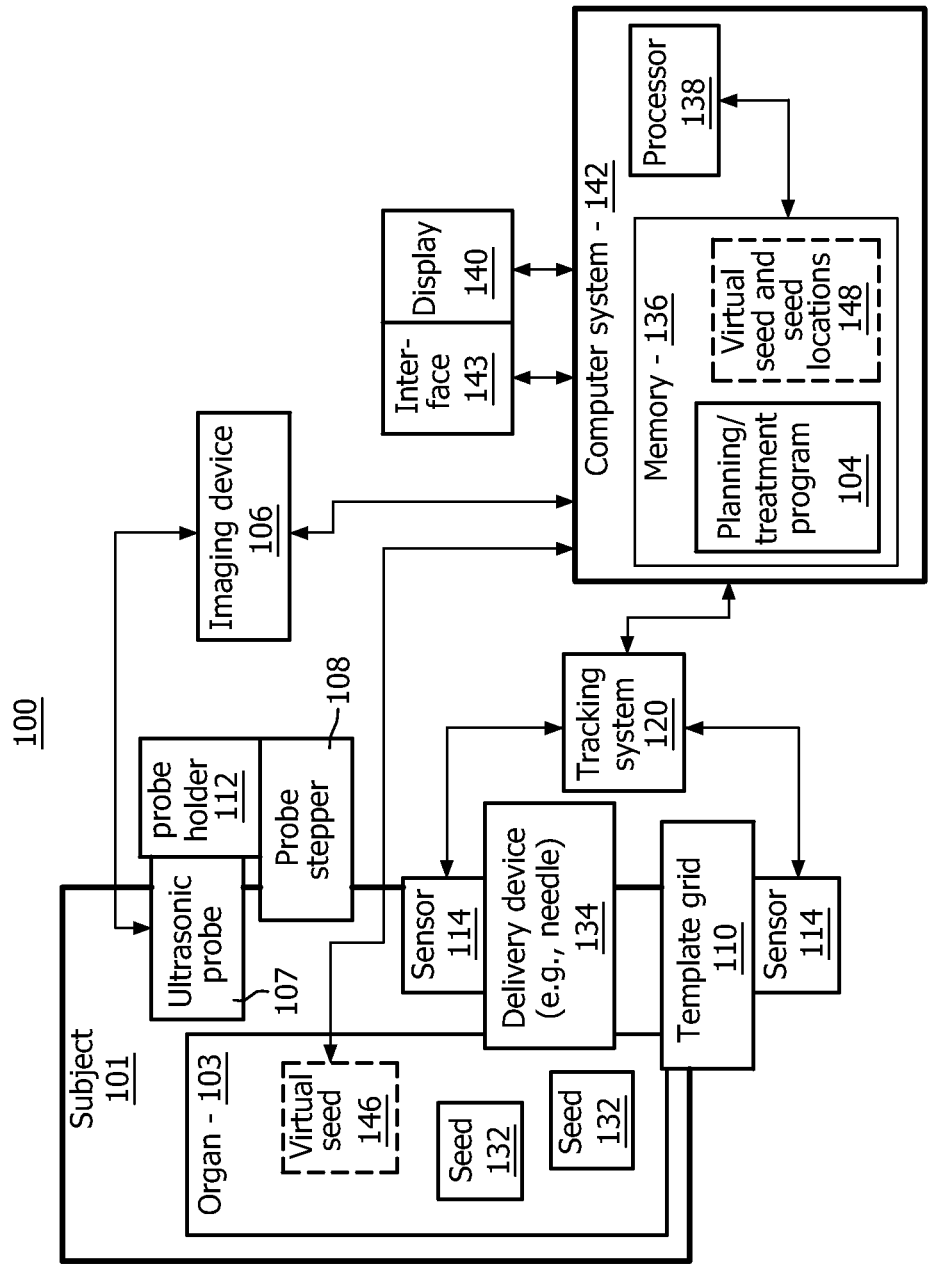
FIG. 1 is a block/flow diagram showing a system/method for implanting treatment elements in accordance with one illustrative embodiment.

The present disclosure provides a real-time localization of seeds and seed delivery needles. Improved visualization of seed delivery needles may include use of electromagnetic (EM) tracking or fiber Bragg grating (FBG) localization which can help physicians guide those devices to planned target locations instead of relying on transrectal ultrasound alone. Even with improved needle visualization, issues such as unwanted needle bending may make it impossible for the physician to guide the needles to their precise target locations, and seeds will therefore not reach their pre-planned locations.

EM- or FBG-localization of the seeds as they are deposited permits for the actual seed locations to be recorded. A planning method can automatically adapt to intra-procedural findings (e.g., recomputed dosage for areas based upon seed locations). A conventional brachytherapy workflow is based primarily on pre-procedural planning followed by post-procedural evaluation, such that intra-procedural variations from the plan are not immediately accounted for. A new planning method in accordance with the present principles is fast enough to be computed many times during the procedure, and so, can be fed with intra-procedural findings of actual seed locations to account for any known plan variations. Visual displays may be generated showing dosage fields in real-time to permit a physician to make dosage decisions and account for contingencies at the time of the procedure.

Conventional planning methods are "forward" algorithms, meaning they require significant user interaction to place virtual seeds and observe the resulting dosimetry patterns. In accordance with the present principles, new inverse methods improve this workflow by permitting a user to define dosimetry targets once, and the virtual or actual seed locations are computed automatically, reducing the amount of user interaction needed. When these components are all combined into a single solution, a new workflow emerges that significantly improves upon current practice.

In addition to the new workflow, other workflows can be realized when seed localization and planning is more tightly integrated. For example, placement of empty needles without seeds may be performed first. The needles may be located with EM, then a planning method can be run using the existing needle locations as a constraint. This can be used to plan either stranded seeds, with the appropriate spacing along the strand, or loose seeds. EM-tracking of needles or seed delivery devices may be employed to monitor organ motion or swelling as a trigger to update three-dimensional (3D) imaging for a new planning data set. Advantages include precise placement of seeds to reduce the dose to critical structures. By doing so, side effects will be reduced. Overdosing will likewise be reduced. Since more accurate navigation can support plans that vary seed densities to achieve higher doses in regions with increased suspicion of cancer, a dose boosting scheme can be provided instead of treating an entire prostate gland or other organ the same.

It should be understood that the present principles will be described in terms of the brachytherapy of the prostate; however, other procedures and organs are contemplated and within the scope of the present invention. For example, the present principles are applicable to low dose rate (LDR) brachytherapy and high dose rate (HDR) brachytherapy of the prostate as well as other organs. The other organs and applications may include, but are not limited to, the breast, gynecological procedures, the lung, the liver, the head and neck, the sarcoma, the pancreas, etc. Also the present principles are applicable to energy deposition methodologies, such as RF ablation, cryoablation, photodynamic therapy, etc.

It also should be understood that the present invention will be described in terms of medical instruments; however, the teachings of the present invention are much broader and are applicable to any instruments employed in tracking, analyzing, treating/repairing complex biological or mechanical systems. In particular, the present principles are applicable to internal tracking procedures of biological systems and devices in all areas of the body such as the lungs, heart, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W) and DVD.

Referring now to the drawings in which like numerals represent the same or similar elements and initially to FIG. 1, a system 100 is illustratively shown to improve the accuracy of treatment device placement (e.g., brachytherapy seeds) via intra-operative seed localization, dosimetry, and adaptive planning in a subject 101 (e.g., a patient). Real-time localization of radioactive seeds 132 and seed delivery devices 134 (e.g., needles, applicators, etc.) is performed using a tracking system 120. The tracking system 120 may include, for example, an electromagnetic (EM) tracking system, a fiber optic shape sensing system (FBG), or other tracking system. The tracking system 120 is preferably used in tandem with adaptive, intra-procedural treatment evaluation and planning. A planning/treatment program or method 104 automatically adapts treatment planning to take intra-procedural findings into account. Treatment evaluation and planning can be done many times during a procedure, so that treatment evaluation and planning can be kept current with intra-procedural findings of actual seed locations, to take into account any detectable plan variations.

Program 104 is preferably stored in memory 136 and works in conjunction with a controller or processor 138. Processor 138 is included in a computer system 142 which controls system functions, executes program 104, generates display images on display 140, manages an interface 143 (which may include input and output devices including the display 140), etc. Tracking system 120 works in conjunction with computer system 142 to track devices/needles 134 and seeds 132. Virtual images of the needles 134 and seeds 132 (virtual seeds 146) may be generated. The virtual images may be compared with the images collected by other means, for example, an ultrasonic image taken using an imaging device 106.

Program 104 provides an improved workflow by implementing an "inverse" method, allowing the user to define dosimetry targets once, and computing virtual seed locations automatically to reduce the amount of user interaction needed. The present embodiments are employed to reduce radiation dose to critical anatomical structures and prevent overdosing. Seed densities may be varied to achieve higher doses in regions with increased suspicion of cancer, instead of, for example, treating an entire prostate gland or other organ 103 in the same way.

The system 100 includes imaging device 106. In one embodiment, the imaging device 106 includes an ultrasound system having an ultrasonic probe 107, e.g., a transrectal probe. An ultrasound probe stepper 108 may be employed to automatically advance/retract the probe 107. A template grid 110 may be employed to assist in determining positions and marking instrument process. Template grid 110 may be a physical grid or a virtual grid generated using computer system 142. Any and all of ultrasound probe 107, a probe holder 112 (to secure the probe), stepper 108 and template grid 110 may be spatially tracked with EM, FBG or other localization system 120. This provides a point(s) of reference which enables a determination of where the needles 134 and hence the seeds 132 are being placed within the body of a subject.

Needles 134 or other seed delivery devices such as a Mick applicator are employed for delivering radioactive seeds 132. The seeds 132 may be loose or stranded. The EM, FBG or other spatial localization system 120 includes sensors 114 built into the seed delivery devices 134 or into guided needles used to map out the spatial localization of untracked devices. The localization system 120 permits the determination of where seeds have been placed. Program 104 includes an adaptive inverse planning method which employs the localization of real seeds to update the plan for the remaining virtual seeds (real seeds to be placed). The recorded seed locations (and/or virtual seed locations) 148 are employed to compute the dosage fields around each seed 132 (or virtual seed) and determine a net effect of all seeds that have been implanted. In addition, program support and applications may be provided where a physician can place a virtual seed 146 at any location to see its effect on the dosage field. The placement of virtual seeds 146 may be employed as a planning tool to plan seed placement. Once the physician determines the desired positions, the seeds 132 may be accurately planted using the tracking system 120 and needles 134 (or other devices). In addition, once some or all of the seeds have been placed, the program 104 can recompute metrics to determine if the desired result has been achieved and if not corrections may be made in real-time. In one embodiment, a warning may be provided for attempts to place a seed that has already been placed or delivered by needle. Signaling (audible or visual) on the template grid 110 may be included to prevent the physician from revisiting a location for seed placement. In addition, the program 104 can provide needle counts and seed placed counting so that an instantaneous tally is provided.

Figure 2:
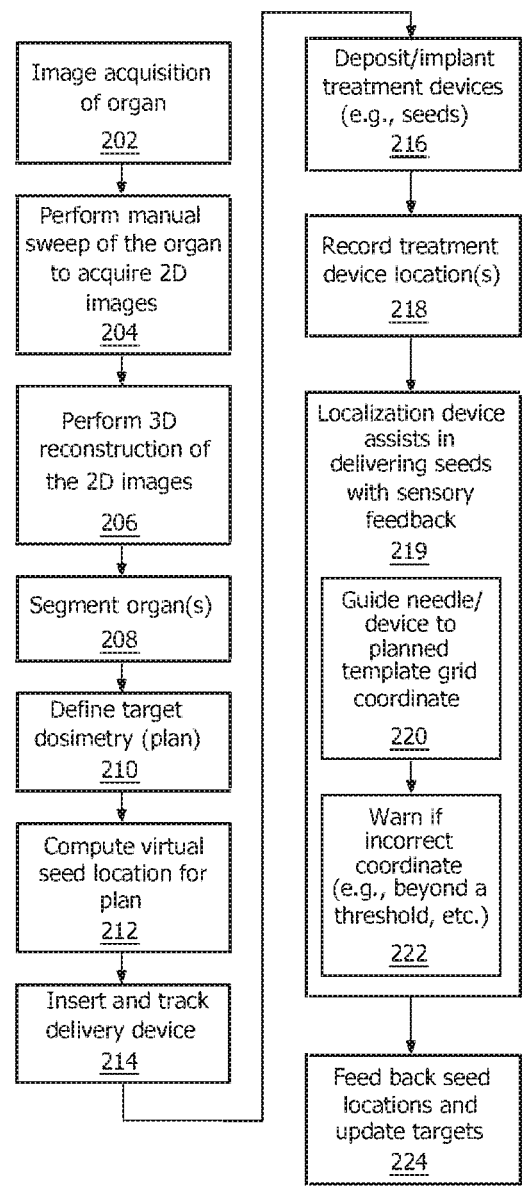
FIG. 2 is a block/flow diagram showing an adaptive implantation procedure in accordance with one illustrative embodiment.

Referring to FIG. 2, in accordance with one embodiment, a method employs the system 100 described in FIG. 1 and includes the stepper 108, ultrasound probe 107, and template grid 110 which have been set up relative to a subject 101. This embodiment is considered fully adaptive. In block 202, a first image acquisition (ultrasound) of an organ (e.g., prostate) and surrounding anatomy is acquired. In block 204, a physician performs a manual (or automatic motorized) sweep of the organ to acquire a set of 2D images. In block 206, a 3D reconstruction is performed from the swept 2D images. In block 208, the prostate and other organs are manually or automatically segmented in the first ultrasound images and/or the 3D ultrasound reconstruction. In block 210, the physician defines target dosimetry (e.g., a plan), for example, desired dose levels for the prostate and surrounding organs at risk. In block 212, the inverse planning method automatically computes the virtual seed locations needed to best reach the physician's dose targets. In the case of stranded seeds, the dosimetrist arranges the seeds and spacers according to the plan.

In block 214, a first seed delivery device (e.g., needle) is inserted into the organ (e.g., prostate). As the needle/device is advanced, its location and/or trajectory is identified on real-time TRUS images using a tracking or localization system (120), along with the target location, helping the physician to best reach that target. In block 216, once the physician has reached the target location or as close as he can get to it, treatment devices (e.g., seeds) are deposited into the prostate or other organ. As this happens, the localization system records the actual seed locations in block 218. In addition to recording seed locations, the localization system may assist in delivering seeds more accurately at the planned locations by providing sensory (e.g., visual (graphical/numerical) and/or audible) feedback about the distance between a planned seed location and the current delivery needle tip position in block 219. In block 220, each delivery needle is guided to its planned template grid coordinate. A visual or audible warning is provided if the needle is inserted in an incorrect grid coordinate providing visual or audible warnings if the needle is bending (beyond a threshold) away from its straight path or if a seed has already been placed at a particular location, etc. in block 222.

In block 224, the actual seed locations are fed back into the planning method (104) so that it can adapt the remaining virtual seed locations to best match/reach the physician's dose targets. Steps 214-224 may be repeated as needed until all seeds have been placed and the desired dose targets have been achieved.

Another method includes an initial fraction of the planning, navigation and seed placement being performed according to a standard workflow without intermediate adaptation but with seed localization in accordance with the present principles. FIG. 3 describes a method for providing seed placement after an initial fraction of seeds have been placed. Referring to FIG. 3, in block 302, recorded seed locations are fed into the adaptive planning program (104) to recompute the virtual seed locations for the remaining seeds. In block 303, a position or pose of the subject is preferably restored to continue implanting seeds.

In block 304, optionally, a spatial localization of an ultrasound probe and stepper facilitate improved feedback when trying to reposition the patient intra-procedurally such that the patient's organ (e.g., prostate) is in a same pose relative to the ultrasound probe and stepper as it was during the pre-planning. This may be achieved by jointly visualizing a "live" real-time ultrasound image of the prostate, and a corresponding MPR (multi-planar reconstruction) of the 3D ultrasound sweep acquired during pre-planning in block 306. In block 308, the corresponding MPR of an organ segmentation from the pre-planning 3D ultrasound is superimposed onto the current "live" real-time ultrasound image. The procedure continues using feedback to place remaining seeds in block 310.

Referring to FIG. 4, another method employs an empty needle placement with constrained planning. In this case, the physician places some fraction of needles without seeds according to his experience and best judgment in block 402. These needles are localized with EM or FBG, and those locations are fed into the planning program to constrain the locations of the virtual seeds in block 404. The physician may also optionally constrain the number of additional needles that would be prescribed by the inverse planning method in block 406. Any additional needles prescribed by the planning method are placed into the organ in block 408. Seeds are placed with the needles according a spacing pattern computed by the planning method in block 410.

Referring to FIG. 5, an organ swelling adaptation method, which can be combined with other embodiments, is illustratively depicted. EM or FBG localization of the needles in the prostate is used to identify swelling of the prostate or other organ, determined by relative movements of the needles, in block 502. If swelling beyond a threshold is identified, a new set of ultrasound images are needed and are acquired to provide to the adaptive planning method, along with the correspondingly updated segmentations of prostate and surrounding organs, in block 504. Block 504 may provide a warning to the user in the form of a volume change for an audible alarm or a visual indicator to indicate that a threshold (e.g., for swelling or movement) has been exceeded. Corrective action may be taken, e.g., restore pose of the patient, anti-inflammatory administered, etc.

In interpreting the appended claims, it should be understood that:
 a) the word "comprising" does not exclude the presence of other elements or acts than those listed in a given claim;
 b) the word "a" or "an" preceding an element does not exclude the presence of a plurality of such elements;
 c) any reference signs in the claims do not limit their scope;
 d) several "means" may be represented by the same item or hardware or software implemented structure or function; and
 e) no specific sequence of acts is intended to be required unless specifically indicated.

Having described preferred embodiments for systems and methods for guided adaptive brachytherapy (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for adaptive placement of treatment elements in an organ of a subject in accordance with a target dosage plan for treatment of the organ, the system comprising:
 a placement device configured to place a treatment element at a first actual location in the organ, the treatment element corresponding to a virtual treatment element at a planned location in a model of the organ;
 a tracking system configured to track the placement of the treatment element by identifying a trajectory of the placement device for guiding a tip of the placement device toward a planned location of the treatment element according to the target dosage plan, and to identify the first actual location at which the treatment element is placed;
 an ultrasound imaging device configured to generate a planning image of the organ with the subject in an initial pose for determining the target dosage plan and to generate a real-time image of the organ after the placement of the treatment element; and
 a computer system comprising:
  computer readable storage media configured to store the first actual location of the treatment element provided by the tracking system; and
  a processor programmed to compute an effect of the treatment element at the first actual location on the target dosage plan for treatment of the organ as compared to an effect of the virtual treatment element at the planned location, to adapt another planned location of another virtual treatment element in the model of the organ in response to the computed effect of the treatment element to achieve the target dosage plan, and to superimpose the planning image onto the real-time image of the organ to enable repositioning of the subject to the initial pose for placing another treatment element,
 wherein the placement device is further configured to place the another treatment element, corresponding to the another virtual treatment element, in a second actual location in the organ corresponding to the adapted another planned location.

2. The system as recited in claim 1, wherein the placement device includes one of a needle, a probe, and an applicator.

3. The system as recited in claim 1, wherein each of the treatment element and the another treatment element includes a radioactive seed.

4. The system as recited in claim 1, wherein each of the virtual treatment element and the another virtual treatment element includes a virtual seed.

5. The system as recited in claim 1, wherein the ultrasound imaging device comprises a transrectal ultrasound (TRUS) device.

6. The system as recited in claim 1, wherein the tracking system includes a fiber Bragg grating system.

7. The system as recited in claim 1, wherein the processor is further programmed to compute a dosage of the another virtual treatment element, and to determine a simulated dosage effect of the another virtual treatment element on the target dosage plan.

8. A treatment method, comprising:
 acquiring an ultrasound planning image of a subject positioned in an initial pose,
 computing virtual seed locations of virtual seeds in a model of the subject in the initial pose to determine a target dosage plan;
 identifying a trajectory of a seed delivery device inserted in the subject to guide the seed delivery device to target locations of actual seeds corresponding to at least some of the virtual seed locations, respectively, determined in the target dosage plan;
 depositing the actual seeds in the subject at or close to the respective target locations using the seed delivery device;
 generating real-time ultrasound images of the subject after depositing the actual seeds in the subject;
 recording actual locations of the deposited actual seeds, using a localization method based on positions of the seed delivery device;

comparing the real-time ultrasound images of the subject with multi-planar reconstruction (MPR) of the acquired ultrasound planning image to enable repositioning of the subject from a current pose to the initial pose; and based on the recorded actual locations of the deposited actual seeds, again computing virtual seed locations in the model of remaining virtual seeds, corresponding to target locations at which the actual seeds were not deposited, in accordance with the target dosage plan, and depositing remaining actual seeds corresponding to the remaining virtual seeds with the subject in the initial pose.

9. The method as recited in claim 8, wherein generating the real-time ultrasound images comprises performing three-dimensional reconstruction of two-dimensional ultrasound images of the subject.

10. The method as recited in claim 9, wherein identifying the trajectory of the seed delivery device includes tracking the seed delivery device using the ultrasound images.

11. The method as recited in claim 8, further comprising:
providing sensory feedback related to distances between the respective target locations and current positions of the seed delivery device, wherein depositing the actual seeds at or close to the respective target locations is based on the sensory feedback.

12. The method as recited in claim 8, further comprising:
providing a template grid for assisting in guiding the seed delivery device to a planned template grid coordinate of each of the actual seeds; and
providing a warning if the seed delivery device is inserted in an incorrect grid coordinate.

13. The method as recited in claim 8, wherein the seed delivery device includes an empty needle without a seed, the method further comprising constraining virtual seeds to a trajectory of the empty needle.

14. The method as recited in claim 13, wherein depositing the actual seeds comprises depositing at least one of the actual seeds at the trajectory of the empty needle.

15. The method as recited in claim 8, further comprising:
determining swelling of an organ of the subject by relative movement of needles of the seed delivery device measured using the localization method; and
when the determined swelling exceeds a threshold, providing a set of ultrasound images for computing new locations of the virtual seeds in the model of the subject to achieve the target dosage plan.

16. The method as recited in claim 8, wherein the localization method comprises electromagnetic (EM) tracking or fiber Bragg grating (FBG) localization.

17. A treatment method, comprising:
placing seeds at actual seed locations in a subject, using a seed delivery device guided by a tracking system, at or close to target locations corresponding to planned virtual seed locations in a model to reach a target dosage plan determined with the subject in an initial pose;
determining the actual seed locations of the seeds in the subject by localizing a tip of the seed delivery device when placing the seeds using the tracking system, and recording the actual seed locations;
computing revised virtual seed locations in the model based on the recorded actual seed locations to provide a dosage in accordance with the target dosage plan;
performing ultrasound imaging of the subject after placing the seeds at the actual seed locations in the subject;
comparing the ultrasound imaging of the subject in a current pose to multi-planar reconstruction (MPR) of an ultrasound planning image of the subject acquired with the subject in the initial pose to enable repositioning of the subject to the initial pose; and
placing additional seeds at additional actual seed locations in the subject at or close to revised target locations corresponding to the revised virtual seed locations, using the seed delivery device guided by the tracking system, with the subject repositioned to the initial pose.

18. The method as recited in claim 17, further comprising providing sensory feedback related to a distance between each target location corresponding to the planned virtual seed location and a current location of the seed delivery device in the subject, wherein providing the sensory feedback includes:
providing a template grid for assisting in guiding the seed delivery device to the target locations corresponding to the virtual planned seed locations, the virtual planned seed locations having corresponding grid coordinates in the template grid; and
providing a warning when the seed delivery device is inserted in an incorrect grid coordinate, different from the corresponding grid coordinates in the template grid.

19. The method as recited in claim 17, wherein the seed delivery device includes an empty needle without a seed, the method further comprising constraining the placing of the additional seeds along a trajectory of the empty needle.

20. The method as recited in claim 17, further comprising:
determining swelling of an organ of the subject by relative movement of needles of the seed delivery device; and
when the determined swelling exceeds a threshold, providing a set of ultrasound images for computing new virtual seed locations in accordance with the target dosage plan.

* * * * *